(12) United States Patent
Zhang et al.

(10) Patent No.: US 10,378,417 B2
(45) Date of Patent: Aug. 13, 2019

(54) METHOD AND SYSTEM FOR EXHAUST PARTICULATE MATTER SENSING

(71) Applicant: Ford Global Technologies, LLC, Dearborn, MI (US)

(72) Inventors: Xiaogang Zhang, Novi, MI (US); Jianwen James Yi, West Bloomfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 206 days.

(21) Appl. No.: 15/479,200

(22) Filed: Apr. 4, 2017

(65) Prior Publication Data

US 2018/0283254 A1    Oct. 4, 2018

(51) Int. Cl.
| | |
|---|---|
| *F01N 13/00* | (2010.01) |
| *G01M 15/02* | (2006.01) |
| *F01N 11/00* | (2006.01) |
| *G01N 15/06* | (2006.01) |
| *G01N 15/00* | (2006.01) |

(52) U.S. Cl.
CPC ............ *F01N 13/008* (2013.01); *F01N 11/00* (2013.01); *G01M 15/02* (2013.01); *G01N 15/0618* (2013.01); *G01N 15/0656* (2013.01); *F01N 2560/05* (2013.01); *F01N 2560/20* (2013.01); *G01N 2015/0046* (2013.01)

(58) Field of Classification Search
CPC .... F01N 13/008; F01N 11/00; F01N 2560/05; F01N 2560/20; G01M 15/02; G01N 15/0618; G01N 15/0656; G01N 2015/0046

USPC ............ 60/274, 277, 297, 311; 73/40, 49.2, 73/114.69, 114.74

See application file for complete search history.

(56) References Cited

U.S. PATENT DOCUMENTS

| | | |
|---|---|---|
| 6,634,210 B1 | 10/2003 | Bosch et al. |
| 8,225,640 B2 | 7/2012 | Nelson et al. |
| 8,341,936 B2 | 1/2013 | Zhang |
| 8,756,913 B2 | 6/2014 | Liu et al. |
| 2013/0031967 A1 | 2/2013 | Ichimasa |
| 2013/0219990 A1 | 8/2013 | Allmendinger et al. |
| 2015/0355066 A1 | 12/2015 | Zhang |
| 2015/0355067 A1 | 12/2015 | Zhang et al. |
| 2016/0131013 A1 | 5/2016 | Yi et al. |
| 2016/0160721 A1 | 6/2016 | Zhang |
| 2016/0223432 A1* | 8/2016 | Kubinski ................. F01N 3/027 |
| 2016/0288038 A1* | 10/2016 | Takaoka ............. B01D 46/0057 |
| 2017/0058746 A1 | 3/2017 | Zhang |
| 2017/0058748 A1* | 3/2017 | Zhang ................. G01N 15/0656 |

(Continued)

OTHER PUBLICATIONS

Zhang, Xiaogang, "Method and System for Exhaust Particulate Matter Sensing," U.S. Appl. No. 14/947,853, filed Nov. 20, 2015, 48 pages.

(Continued)

*Primary Examiner* — Patrick D Maines
*Assistant Examiner* — Dapinder Singh
(74) *Attorney, Agent, or Firm* — Julia Voutyras; McCoy Russell LLP

(57) ABSTRACT

Methods and systems are provided for a particulate matter sensor arranged along an exhaust passage. In one example, a particulate matter sensor includes a series of tubes arranged in substantially a U-shape, and where the particulate matter sensor comprises one or more of a rotating element and a temperature sensing element.

5 Claims, 8 Drawing Sheets

(56) References Cited

U.S. PATENT DOCUMENTS

2017/0074148 A1\* 3/2017 Zhang .................. F01N 13/008
2017/0102311 A1 4/2017 Zhang

OTHER PUBLICATIONS

Zhang, Xiaogang, "Method and System for Exhaust Particulate Matter Sensing," U.S. Appl. No. 15/062,384, filed Mar. 7, 2016, 57 pages.
Zhang, Xiaogang, "Method and System for Exhaust Particulate Matter Sensing," U.S. Appl. No. 15/145,117, filed May 3, 2016, 64 pages.
Zhang, Xiaogang, "Method and System for Exhaust Particulate Matter Sensing," U.S. Appl. No. 15/290,893, filed Oct. 11, 2016, 51 pages.

\* cited by examiner

US 10,378,417 B2

METHOD AND SYSTEM FOR EXHAUST PARTICULATE MATTER SENSING

FIELD

The present description relates generally to a particulate matter (PM) sensor.

BACKGROUND/SUMMARY

Engine emission control systems may utilize various exhaust sensors. One example sensor may be a particulate matter sensor which indicates particulate matter mass and/or concentration in exhaust gas. In one example, the particulate matter sensor may operate by accumulating particulate matter over time and providing an indication of the degree of accumulation as a measure of exhaust particulate matter levels.

Particulate matter sensors may correlate a measured change in electrical conductivity (or resistivity) between a pair of electrodes placed on a substrate surface of the sensor with the amount of particulate matter deposited between the electrodes. Particulate matter sensors may encounter problems with non-uniform deposition of soot on the sensor due to a bias in flow distribution across the surface of the sensor. Further, particulate matter sensors may be prone to contamination from an impingement of water droplets and/or larger particulates present in the exhaust gases. This contamination may lead to errors in sensor output.

Other attempts to address particulate matter sensor performance include guiding a portion of exhaust toward the particulate matter sensor. One example approach is shown by Liu et al. in U.S. Pat. No. 8,756,913. Therein, a pair of intersecting tubes are located along an exhaust passage with a sensor located in an upper portion of the exhaust passage fluidly coupled to an axial tube of the pair of tubes. The tubes are configured to receive exhaust gas from a variety of locations within the exhaust passage to increase an accuracy of data provided by the sensor.

However, the inventors herein have recognized potential issues with such systems. As one example, the pair of tubes may conduct large particulate matter and/or water droplets onto the sensor. This may decrease a reliability of data provided by the sensor with regards to PF degradation.

In one example, the issues described above may be addressed by a method comprising rotating a screen of a particulate matter sensor periodically via an actuator and indicating leakage of a particulate filter based on an amount of power supplied to the actuator. In this way, the amount of power supplied to the actuator increases as particulate matter increases friction experienced by the screen during the periodic rotations.

As one example, the screen is rotated against a filter in the particulate matter sensor each fixed period interval. The screen is rotated a threshold angle, wherein an amount of power supplied to the screen is monitored. The screen is rotated back to its original starting position and the filter is regenerated back to a state comprising less particulate matter stored thereon. By doing this, the filter in the particulate matter sensor may comprise a substantially similar amount of particulate matter following the rotation of the screen. The particulate matter sensor is located downstream of a particulate matter filter located in the exhaust passage. The particulate matter filter undergoes regenerations to enable the particulate matter filter to continue to capture particulate matter. However, the particulate matter filter may degrade following multiple regeneration events experienced over time. The degradation may include one or more of cracks, leaks, and holes. As such, a greater amount of particulate matter may flow to the filter in the particulate matter sensor, thereby increasing an amount of power needed to rotate the screen. If the amount of power exceeds a threshold amount of power, then the particulate matter filter in the exhaust passage may be degraded.

As another example, additionally or alternatively, the particulate matter sensor does not include a screen. However, the particulate matter sensor is configured to regenerate the filter each fixed period interval, as described above. Over time, the particulate matter filter in the exhaust passage becomes degraded. This may result in higher regeneration temperatures experienced by the filter in the particulate matter sensor. As such, the particulate matter filter in the exhaust passage may be degraded when a regeneration temperature of the filter in the particulate matter sensor is greater than a threshold temperature.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2-3 and 6 are shown approximately to scale.

DETAILED DESCRIPTION

Figure 1:
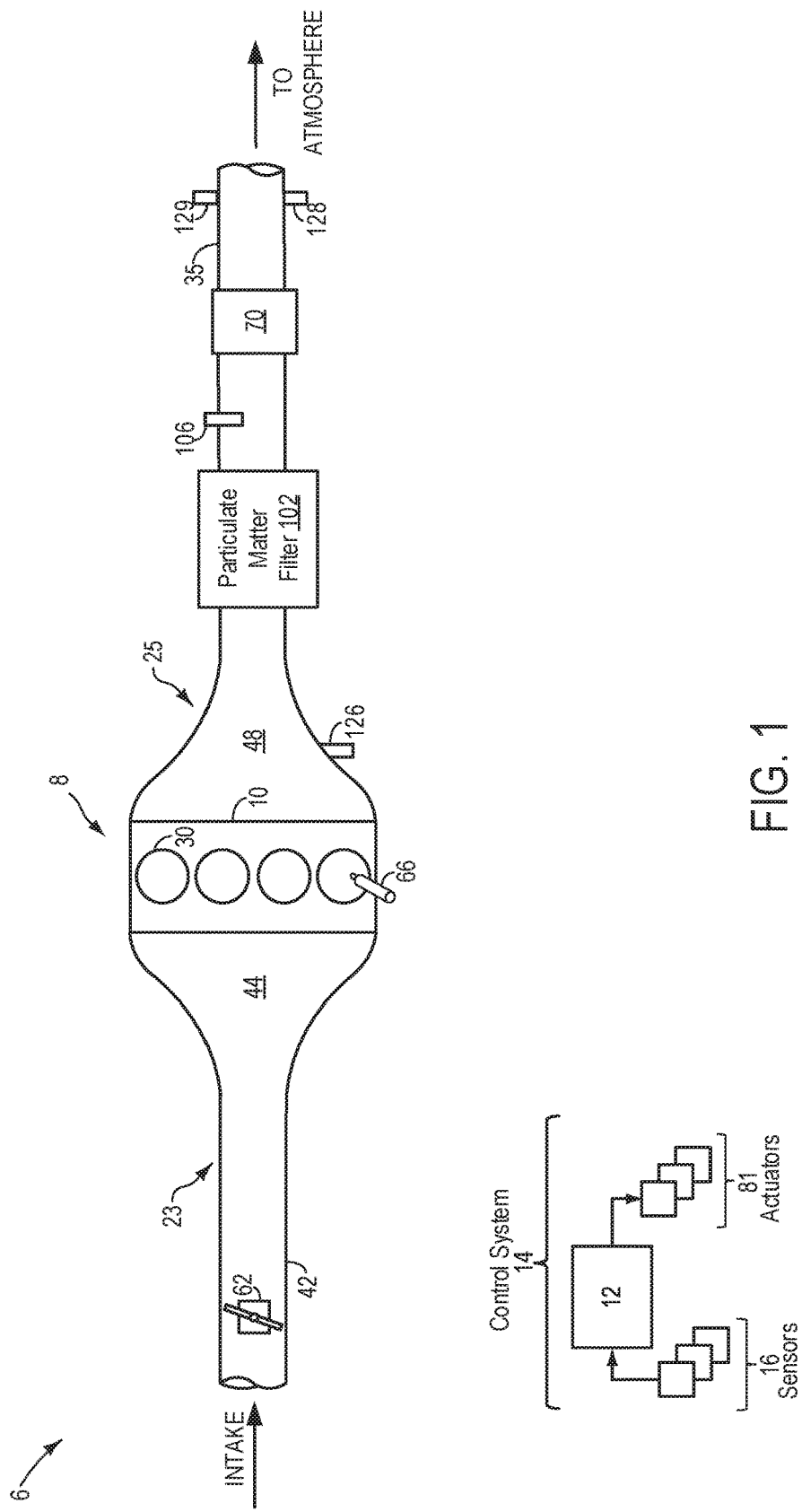
FIG. 1 shows a schematic diagram of an engine and an associated particulate matter (PM) sensor arranged along an exhaust passage.
Figure 2:
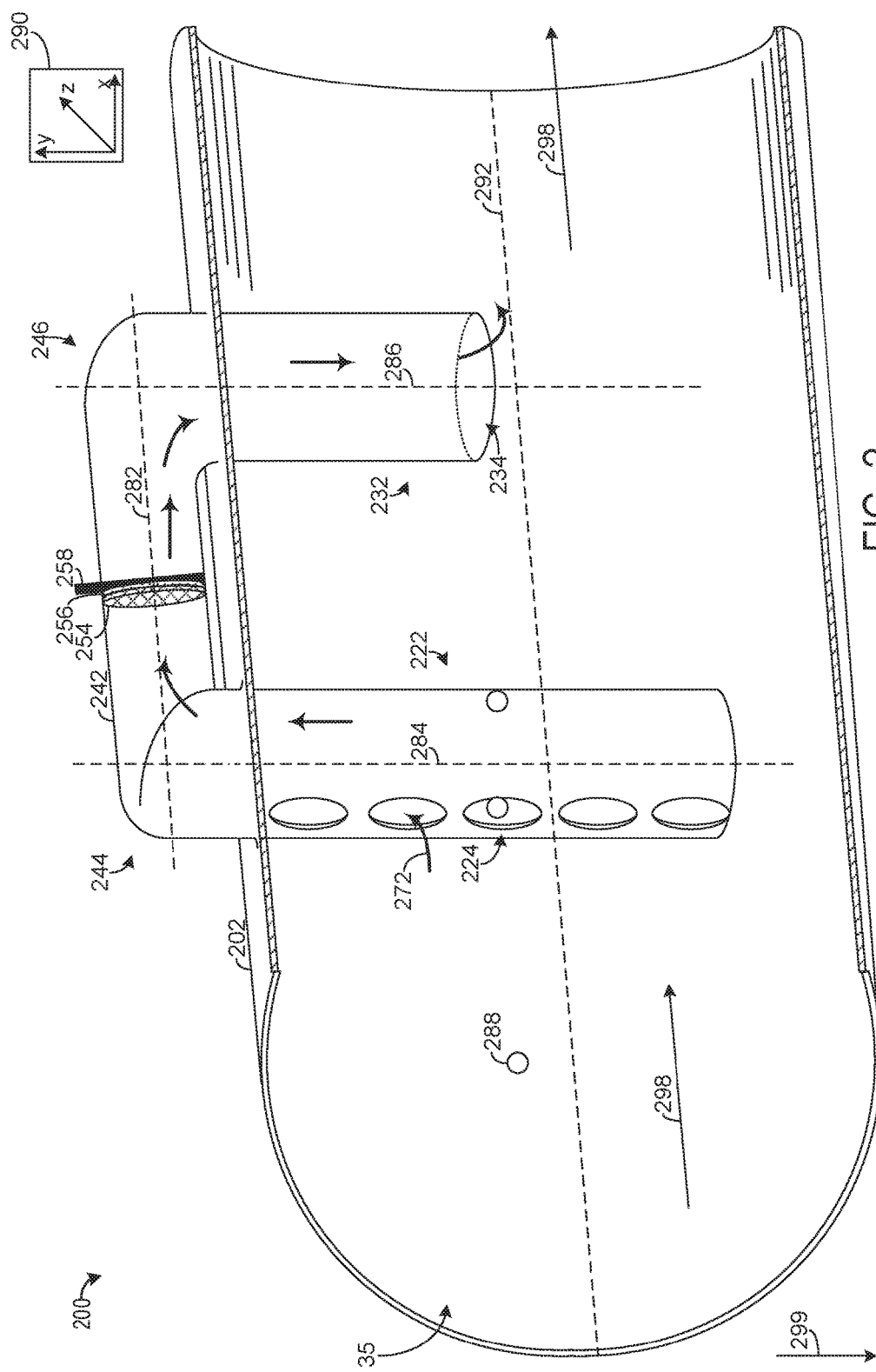
FIG. 2 shows a first embodiment of the PM sensor.

The following description relates to systems and methods for a particulate matter (PM) sensor. The PM sensor is arranged along an exhaust passage downstream of a particulate filter, as shown in FIG. 1. A first embodiment of the PM sensor is illustrated in FIG. 2, wherein the PM sensor includes a rotatable screen and a heating element pressed against opposite surfaces of a filter. The filter is sandwiched between the screen and the heating element, as shown in FIG. 3A. A method for periodically rotating the screen and measuring a power needed to rotate the screen to a threshold angle is described in FIG. 4. If the power needed to rotate the screen to the threshold angle is greater than a threshold power, then the particulate matter filter in the exhaust passage upstream of the PM sensor may be degraded. An operating sequence illustrating conditions in the PM sensor is shown in FIG. 5.

Figure 6:
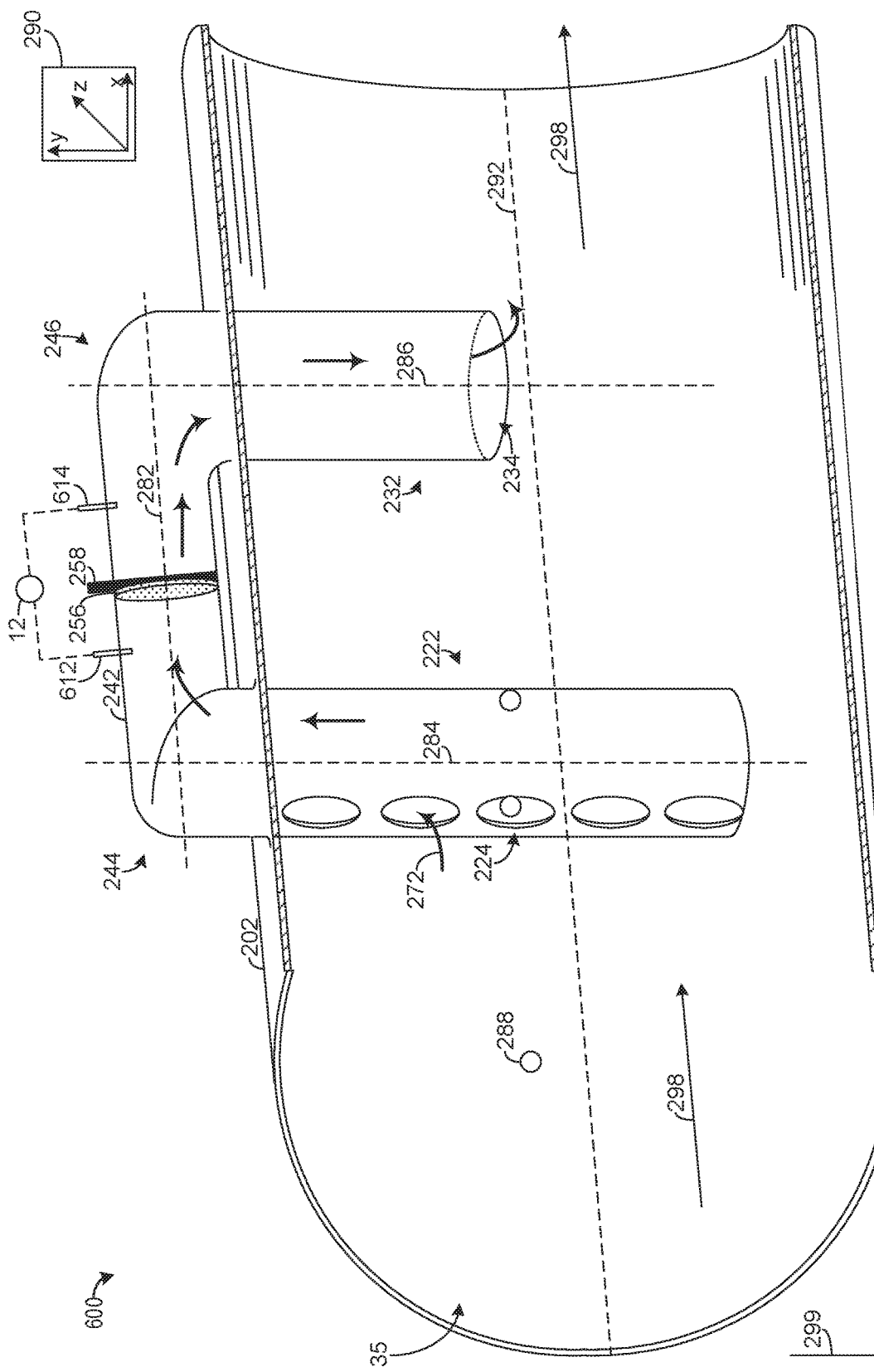
FIG. 6 shows a second embodiment of the PM sensor.
Figure 7:
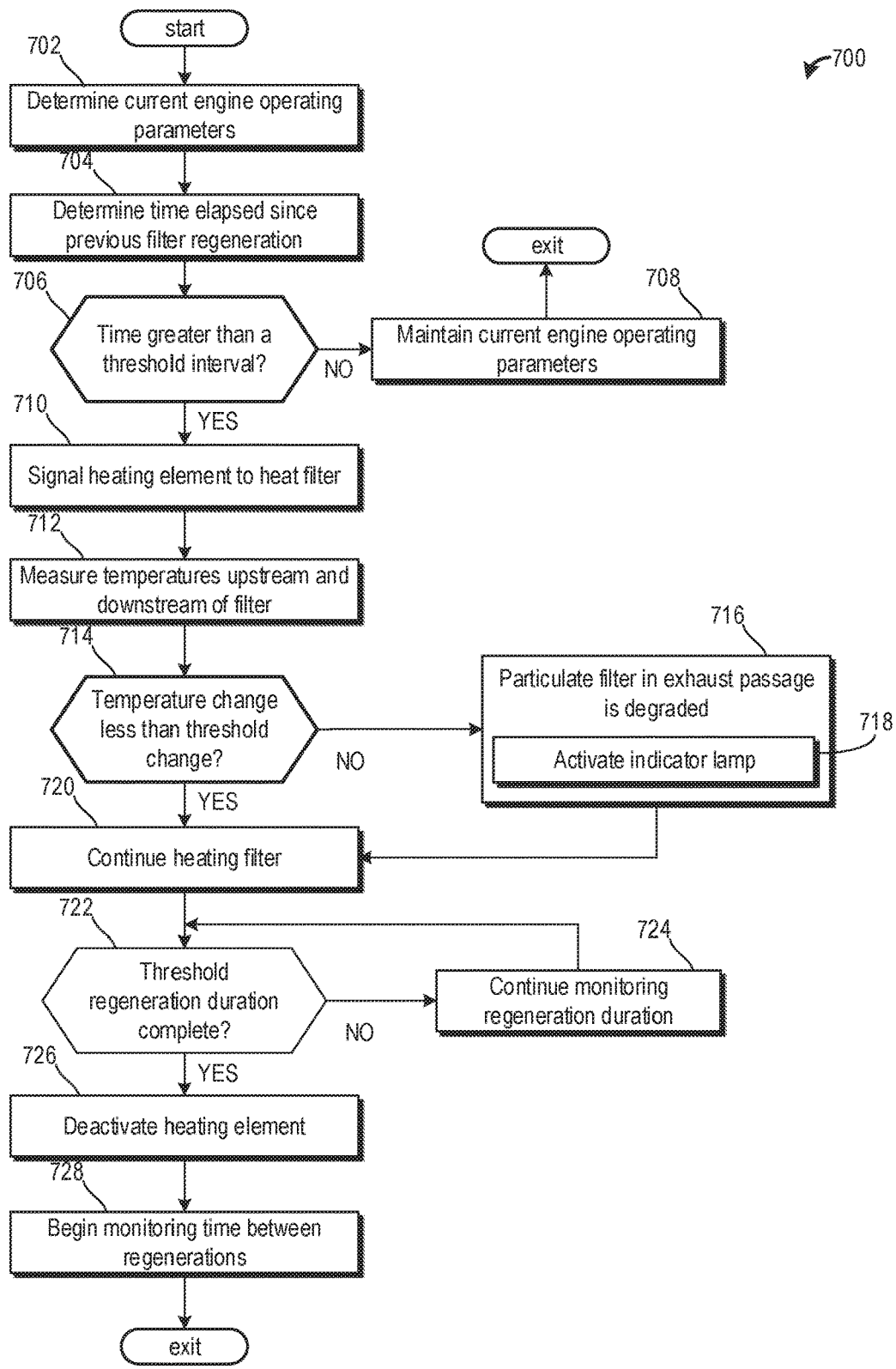
FIG. 7 shows a method for operating the heating element of the second embodiment and determining degradation of the particulate filter based on a regeneration temperature measured in the PM sensor.
Figure 8:
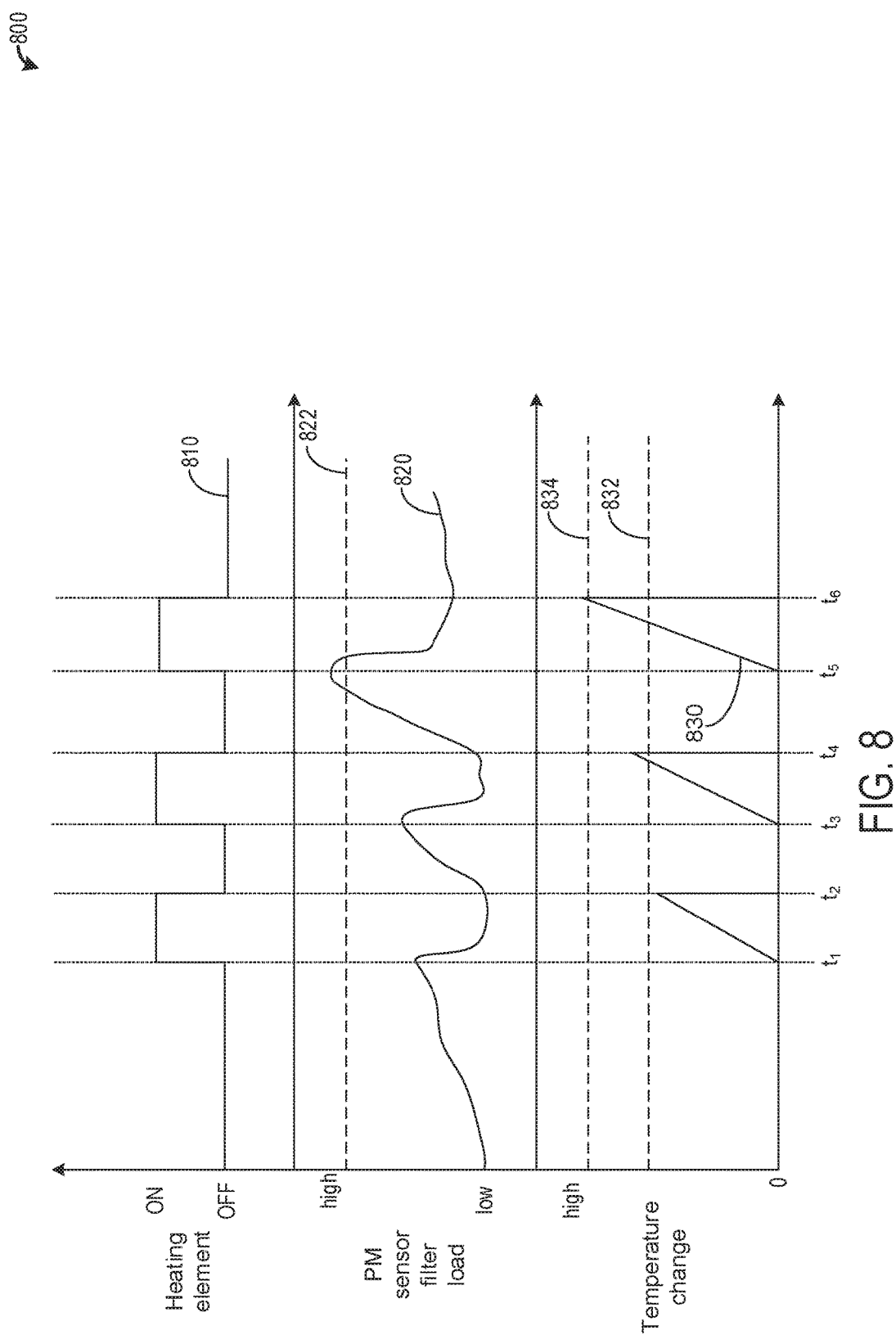
FIG. 8 shows an engine operating sequence illustrating PM sensor condition changes over time.

A second embodiment of the PM sensor is illustrated in FIG. 6, wherein the second embodiment includes one or more temperature sensors located proximally to the filter in the PM sensor. In one example, there are two temperature sensors, with one of the temperature sensors located upstream of the filter and a second of the temperature sensors located downstream of the filter. A method for comparing feedback from the temperature sensors is shown in FIG. 7. In one example, the comparison may determine if a particulate matter filter in the exhaust passage is degraded. An operating sequence illustrating conditions in the PM sensor is shown in FIG. 8.

FIGS. 1-3, and 6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include particulate matter filter 102, which temporarily filters PMs from entering gases, positioned upstream of emission control device 70. In one example, particulate matter filter 102 a diesel particulate matter retaining system. Particulate matter filter 102 may have a monolith structure made of, for example, cordierite or silicon carbide, with a plurality of channels inside for filtering particulate matter from diesel exhaust gas. Tailpipe exhaust gas that has been filtered of PMs, following passage through particulate matter filter 102, may be measured in a PM sensor 106 and further processed in emission control device 70 and expelled to the atmosphere via exhaust passage 35. As shown, the PM sensor 106 is arranged downstream of the particulate matter filter 102 in the exhaust passage 35. Additionally, the PM sensor 106 comprises a filter functionally similar to the particulate matter filter 102, however, the filter in the PM sensor 106 is smaller than the particulate matter filter 102. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

Additionally or alternatively, components of the PM sensor are rotated and/or regenerated periodically responsive to operating conditions of the engine and/or exhaust system. Components may include one or more of a screen and a filter. In one example, the conditions may include a time elapsed since a previous rotation and/or regeneration, miles driven, estimated particulate matter leaked, etc. as will be described in greater detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor opening (e.g., controller opening of a valve or plate in an inlet of the PM sensor), etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller.

In one example, the controller comprises instructions stored thereon that when executed enable the controller to regenerate the filter located in the PM sensor 106. In one example, additionally or alternatively, the controller signals to an actuator to rotate a screen located in the PM sensor 106 prior to the regeneration. The regeneration may occur in response to a threshold duration of time passing. The threshold duration may be a fixed period interval substantially equal to 10 minutes. It will be appreciate by those skill in the art that other amount of time may be used without departing from the scope of the present disclosure. By measuring either the power needed to rotate the screen or a temperature of the regeneration in the PM sensor 106, the particulate matter filter 102 may be determined to be degraded or function as desired. Degradation may include the particulate matter filter developing one or more cracks, leaks, and holes.

Turning now to FIG. 2, it shows a first embodiment 200 of the PM sensor 106 arranged in the exhaust passage 35 of FIG. 1. As such, components previously introduced may be similarly numbered in subsequent figures. As described above, the PM sensor 106 is located downstream of a particulate filter (e.g., particulate filter 102 of FIG. 1). The PM sensor 106 is configured to receive and store a portion of particulate matter flowing through the particulate filter. The PM sensor 106 may diagnose a condition of the particulate filter based on an amount of particulate matter captured by the PM sensor 106.

An axis system 290 comprises three axes, namely an x-axis parallel to the horizontal direction, a y-axis parallel to a vertical direction, and a z-axis perpendicular to both the x- and y-axes. A direction of gravity is shown by arrow 299 and is parallel to the y-axis. A general direction of exhaust gas flow through the exhaust passage 35 is shown via arrows 298 parallel to the x-axis. A central axis of the exhaust passage 35 and/or exhaust pipe 202 is shown via dashed line 292. As such, dashed line 292 may be herein referred to as central axis 292.

The PM sensor 106 may be comprised of one or more of aluminum, copper, iron, carbon fiber, magnesium, steel, and other materials suited for an exhaust gas environment. In some examples, surfaces of PM sensor 106 may be coated to prevent PM impinging thereon. It will be appreciated that unless otherwise noted, surfaces of the PM sensor 106 are impervious to exhaust gas flow. In this way, there are no additional inlets or other outlets other than those described herein. In one example, for a vehicle with wheels on the ground, the PM sensor 106 is coupled to a top of the exhaust pipe 202 furthest away from the ground.

The first embodiment 200 of the PM sensor 106 is shown as a substantially U-shaped tube. In one example, the PM sensor 106 is asymmetric, wherein an upstream pipe 222 is longer along the y-axis than a downstream pipe 232. It will be appreciated that features described herein as upstream of or downstream of are described with respect to the direction of exhaust gas flow. As such, exhaust gas reaches the upstream pipe 222 before the downstream pipe 232. As shown, the upstream pipe 222 extends into the exhaust passage 35 to a location below the central axis 292 along the y-axis. However, the downstream pipe 232 extends into the exhaust passage 35 to a located above the central axis 292 along the y-axis. In some examples, additionally or alternatively, the upstream pipe 222 and downstream pipe 232 may be substantially equal in height (e.g., a length along the y-axis). Additionally or alternatively, the PM sensor 106 may be other shapes without departing from the scope of the present disclosure. For example, the PM sensor 106 may be a C-shape, V-shape, and J-shape.

A connecting pipe 242 is physically coupled to the upstream pipe 222 and the downstream pipe 232. Specifically, the connecting pipe 242 is physically coupled to the upstream pipe 222 at upstream bend 244. Likewise, the connecting pipe 242 is physically coupled to the downstream pipe 232 at downstream bend 246. The connecting pipe 242 may be physically coupled to the upstream pipe 222 and the downstream pipe 232 via fusions, welds, adhesives, and/or a combination thereof. The connecting pipe 242 is parallel to the x-axis and perpendicular to the upstream 222 and downstream 232 pipes.

The connecting pipe 242, upstream bend 244, and downstream bend 246 are located entirely outside of the exhaust pipe 202. The upstream pipe 222 extends from the upstream bend 244, through a cutout of the exhaust pipe 202, and into the exhaust passage 35 to a depth below the central axis 292. Welds, fusions, adhesives, or a combination thereof may physically couple the upstream pipe to the exhaust pipe 202. Additionally, these coupling elements hermetically seal an intersection between the upstream pipe 222 and the exhaust pipe 202 such that exhaust gas may not flow through the intersection to an ambient atmosphere and/or engine. The downstream pipe 232 extends from the downstream bend 246, through a cutout of the exhaust pipe 202, and into the exhaust passage 35 to a depth above the central axis 292. Welds, fusions, adhesives, or a combination thereof may physically couple the downstream pipe 232 to the exhaust pipe 202. Additionally, these coupling elements hermetically seal an intersection between the downstream pipe 232 and the exhaust pipe 202 such that exhaust gas may not flow through the intersection to the engine and ambient atmosphere. In this way, exhaust gas only flows from the exhaust passage 35 to an ambient atmosphere via a tailpipe.

A diameter of the exhaust pipe 202 is larger than diameters of the upstream 222, downstream 232, and connecting 242 pipes. The diameters of the upstream 222, downstream 232, and connecting 242 pipes may be substantially equal such that the PM sensor 106 has a single diameter. It will be appreciated that diameters of the pipes of the PM sensor 106 may be unequal without departing from the scope of the present disclosure. In this way, the PM sensor 106 may be a contiguous device.

The upstream pipe 222 comprises a plurality of perforations 224 configured to admit exhaust gas into a first passage housed in the upstream pipe 222. The perforations 224 face an upstream direction opposite to the direction of incoming exhaust gas flow. As such, exhaust gas may uninterruptedly flow through the perforations 224 and into the first passage of the upstream pipe 222. The perforations 224 are aligned along a common axis parallel to a central axis 284 of the upstream pipe 222. In one example, there are exactly five perforations. However, it will be appreciated that there may be greater than or fewer than five perforations 224 without departing from the scope of the present disclosure. For example, an opening of the perforations 224 may be reduced to incorporate a greater number of perforations 224 on the upstream face of the upstream pipe 222. The perforations 224 are elliptical, in one example. However, the perforations 224 may be other shapes, for example, square-shaped, circular, rectangular, or triangular, without departing from the scope of the present disclosure. In one example, the perforations 224 is the only element of the first pipe 222 fluidly coupling an interior of the first pipe 222 to the exhaust passage 35.

The first passage of the upstream pipe 222 is configured to receive exhaust gas from the exhaust passage 35 and conduct the exhaust gas in a direction opposite gravity 299 to the connecting pipe 242, outside the exhaust passage. However, the first passage of the upstream pipe 222 is also configured to prevent flow of large particulates (e.g., water droplets and/or large particulate matter) to the connecting pipe 242. Large particulates may obfuscate PM sensor 106 measurements. Several factors may limit the flow of large particulates to the connecting pipe 242. First, gravity pushes the large particulates in a downward direction away from the connecting pipe 242. Second, a distance between the upstream surface, where the perforations 224 are located, and the downstream surface of the upstream pipe 222 is sized such that a momentum of large particulates carries the large particulates into the downstream surface. As such, the large particulates may impinge onto the downstream surface and therefore do not flow into the connecting pipe 242. In the embodiment 200, the first pipe 222 is sealed at a bottom surface 226. In this way, large particulates may accumulate at the bottom of the first pipe 222 and burn when exhaust gas temperatures are sufficiently hot (e.g., greater than 600° C.). However, it will be appreciated that the bottom surface 226 may comprise an opening for draining large particulates out of the first passage of the upstream pipe 222 in alternate embodiments.

The connecting pipe 242 comprises a second passage configured to receive exhaust gas from the first passage of the upstream pipe 222. The second passage of the connecting pipe 242 flows exhaust gas in a direction substantially parallel to the direction of incoming exhaust gas flow. However, exhaust gas in the second passage of the connecting pipe flows outside of the exhaust passage 35, separately from exhaust gas in the exhaust passage 35.

A screen 254, a filter 256, and a heating element 258 are cascaded along a horizontal axis 282 of the second passage of the connecting pipe 242. In one example, the horizontal axis 282 is a central axis of the connecting pipe 242, and is parallel to the central axis 292 of the exhaust pipe 202. The screen 254 is arranged upstream of the filter 256, which is arranged upstream of the heating element 258. The screen 254 is in face-sharing contact with the filter 256 and the filter 256 is in face-sharing contact with the heating element 258. In this way, the filter 256 is sandwiched between the screen 254 and the heating element 258.

The screen 254 is porous and configured to allow exhaust gas to flow directly therethrough to the filter 256. The screen 254 is incapable of capturing PM in the exhaust gas flow. As such, particulates do not accumulate onto any surfaces of the screen 254. In one example, the screen is a wire-mesh. However, the screen 254 may be corrugated or other similar shapes in alternative embodiments.

The filter 256 is honeycomb-shaped in one example, to allow exhaust gas to flow therethrough while also being configured to capture PM in the exhaust gas flow. As such, particulates accumulate onto surfaces of the filter 256. Particulates stored on the filter 256 may contact surfaces of the screen 254. The screen 254 is configured to rotate about the horizontal axis 282 to a threshold angle during certain operating conditions. The PM stored on the filter 256 may increase frictional forces applied to the screen 254, wherein a power needed to rotate the screen 254 to a desired position is proportional to an amount of PM stored on the filter 256. In one example, the power may be electric, mechanical (e.g., hydraulic), and/or a combination thereof. Thus, as the power needed to rotate the screen to the threshold angle increases, then the amount of PM stored on the filter 256 increases. In some examples, the screen 254 is rotated based on a fixed period interval (e.g., every 10 minutes of accumulated engine operation) to measure an amount of PM stored on the filter 256. Subsequent rotation of the screen 254, the heating element 258 is activated to burn PM stored on the filter 256. In this way, the filter 256 is reset to a less loaded state configured to capture more PM. This will be described in greater detail below with respect to FIG. 4.

Exhaust gas flows from the second passage of the connecting pipe 242 to a third passage of the downstream pipe 232. Exhaust gas reenters the boundaries of the exhaust pipe 202 and flows out of the downstream pipe 232 via outlet 234. In this way, the downstream pipe 232 is open at an extreme end proximal to the central axis 292 via the outlet 234.

Specifically, curly headed arrows 272 indicate a direction of exhaust gas flow relative to the PM sensor 106. Additionally, circles 288 indicate a direction of large particulates and/or water droplets flow relative to the PM sensor 106. As shown, exhaust gas and large particulates and/or water droplets enter the upstream pipe 222 via perforations 224 in a direction substantially parallel to the central axis 292. Larger particulates and/or water droplets continue to flow in the direction substantially parallel to the central axis 292 and impinge onto a downstream surface of the upstream pipe 222. In some examples, the upstream pipe 222 comprises an opening similar to outlet 234 of the downstream pipe 232 such that larger particulates and/or water droplets may flow out of a bottom of the upstream pipe 222 below the central axis 292 via the opening and reenter the exhaust passage 35. In this way, larger particulates and/or water droplets may not impinge onto.

Exhaust gas turns after it enters the first passage of the upstream pipe 222 and flows in a direction parallel to an upstream vertical axis 284 opposite gravity 299. In one example, the upstream vertical axis 284 is a central axis of the upstream pipe 222. The exhaust gas flows outside of a boundary of the exhaust pipe 202 and flows into the second passage of the connecting pipe 242. Specifically, after flowing outside a boundary of the exhaust pipe 202, the exhaust gas turns and flows in a direction parallel to the horizontal axis 282, which is parallel to the central axis 292 of the exhaust passage 35. In this way, exhaust gas in the exhaust passage 35 and exhaust gas in the connecting pipe 242 flow in substantially parallel directions. As shown, the upstream vertical axis 284 is substantially perpendicular to the horizontal axis 282. Thus, exhaust gas turns substantially 90 degrees as it flows from the upstream pipe 222 to the connecting pipe 242.

Exhaust gas flows through the screen 254, filter 256, and heating element 258 prior to flowing to the downstream pipe 232. The filter 256 is configured to collect PM from exhaust gas flowing therethrough. As such, exhaust gas upstream of the filter 256 comprises more PM than exhaust gas downstream of the filter 256.

Exhaust gas in the downstream pipe 232 flows in a direction substantially parallel to a downstream vertical axis 286 with gravity 299. In one example, the downstream vertical axis 286 is a central axis of the downstream pipe 232. Additionally, the downstream vertical axis 286 is parallel to the upstream vertical axis 284 and perpendicular to the central axis 292 and horizontal axis 282. As such, exhaust gas turns substantially 90 degrees as it flows from the connecting pipe 242 to the downstream pipe 232. Exhaust gas flows out of the PM sensor 106 by exiting the downstream pipe 232 via the outlet 234. Exhaust gas turns substantially 90 degrees as it flows through the outlet 234 and mixes with exhaust gas in the exhaust passage 35. In this way, exhaust gas flow through the PM sensor 106 is substantially U-shaped in the embodiment of FIG. 2.

Turning now to FIG. 3A, it shows an exploded view 300 of the screen 254, filter 256, and heating element 258 separated from one another. The screen 254, filter 256, and heating element 258 are cascaded along the horizontal axis 282 of the connecting pipe (e.g., connecting pipe 242 of FIG. 2).

The screen 254 is cylindrical with an upstream surface 312, a downstream surface 314, and an outer annular surface 316. The upstream surface 312 faces a direction opposite a direction of incoming exhaust gas flow in the connecting pipe. The downstream surface 314 faces the filter 256 and is pressed against the filter 256 when the PM sensor (e.g., PM sensor 106 of FIGS. 1 and 2) is fully assembled. The outer annular surface 316 is in face-sharing contact and physically coupled to an interior surface of the connecting pipe. In this way, all exhaust gas flowing through the connecting passage flows through the screen 254.

An actuator 304, including a rotating shaft 306, is coupled to the screen 254. Specifically, the rotating shaft 306 is physically coupled to the actuator 304 and to the screen 254 via opposite extreme ends. The rotating shaft 306 is configured to rotate the screen 254 based on power supplied from the actuator 304 in response to instructions from a controller 12. Specifically, the rotating shaft 306 rotates the screen 254 about the horizontal axis 282 by a threshold angle, as will be described in greater detail with respect to FIG. 3B. The actuator 304 may be electric, mechanical, or a combination of both.

The filter 256 is cylindrical with an upstream surface 322, a downstream surface 324, and an outer annular surface 326. In one example, the filter 256 is similarly sized (e.g., substantially equal diameter and width) to the screen 254. Alternatively, the filter 256 and screen 254 are differently sized without departing from the scope of the present disclosure. For example, the filter 256 is larger than the screen 254. The upstream surface 322 faces the screen 254 and is in face-sharing contact with the downstream surface 314 when the PM sensor (e.g., PM sensor 106 of FIG. 2) is fully assembled. The downstream surface 324 faces the heating element 258 and is in face-sharing contact with the heating element when the PM sensor is fully assembled. The heating element is configured to warm-up in response to instructions from the controller 12. PM on the filter 256 may begin to burn at a threshold temperature (e.g., greater than or equal to 600° C.). As such, the filter 256 may return to a less-loaded state as PM burns off and is swept through the connecting pipe as exhaust gas flows therethrough. In this way, the filter 256 returns to a state configured to capture more PM as PM is burned off the filter 256 with assistance from the heating element 258.

Figure 3B:
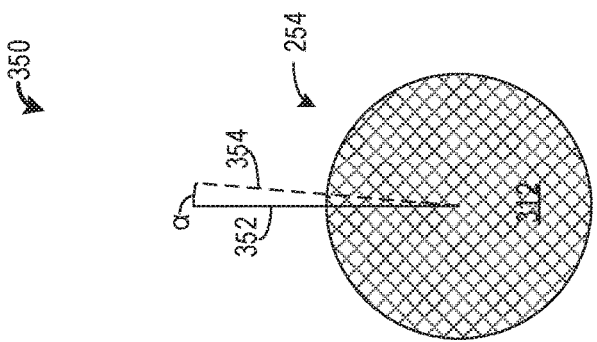
FIGS. 3A and 3B show exploded views of a screen, filter, and heating element arranged in the first embodiment of the PM sensor.
Figure 3A:
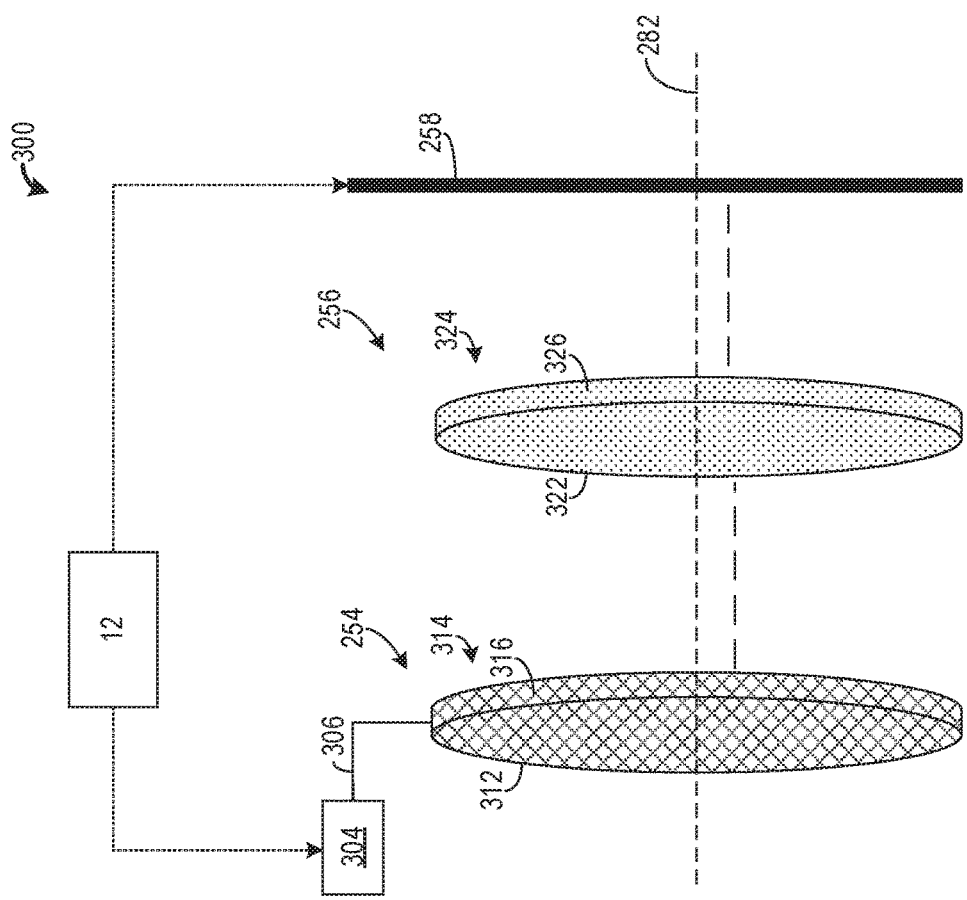

Turning now to FIG. 3B, it shows a view 350 in an upstream-to-downstream direction along the horizontal axis 282 toward the screen 254. Solid line 352 indicates a starting position of the rotating shaft (e.g., rotating shaft 306 of FIG. 3A). Dashed line 354 indicates a final position of the rotating shaft following a rotation of the screen 254. An angle α represents a threshold angle and is between 2-15 degrees. In one example, the angle α (e.g., threshold angle) is equal to exactly five degrees. Following rotation of the screen 254 to the final position in the clockwise direction, the screen 254 is rotated in the counterclockwise direction and returns to the starting position.

In one example, an amount of power (e.g., voltage) needed to rotate the screen 254 from the starting position to the final position in a clockwise direction is monitored. The amount of power may be proportional to an amount of PM stored on the filter 256. This may be due to the PM increasing frictional forces between the filter 256 and the screen 254. If the amount of power needed to rotate the screen the threshold angle is greater than a threshold amount of power, then the particulate filter in the exhaust passage upstream of the PM sensor may be degraded. This will be described in greater detail below.

Figure 4:
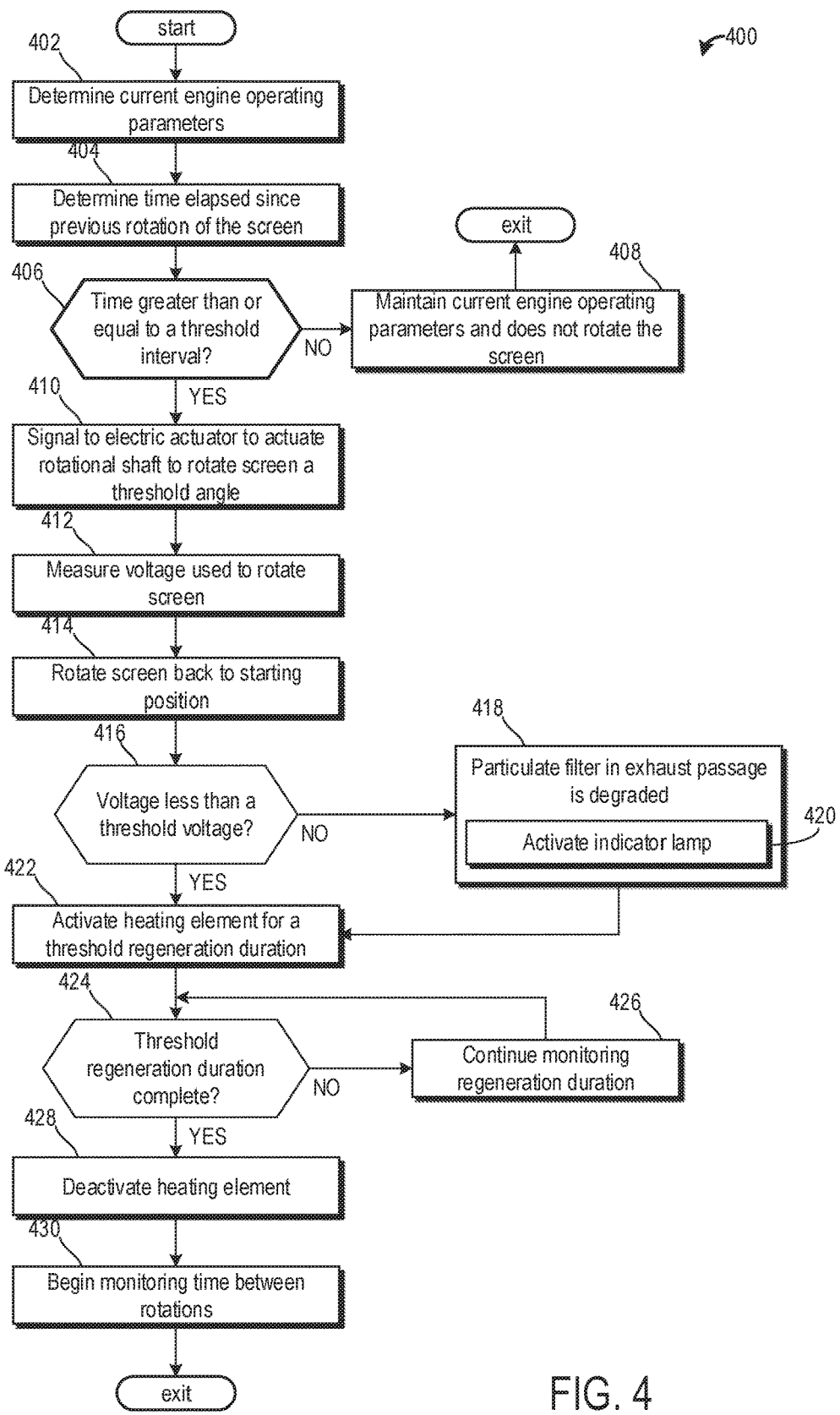
FIG. 4 shows a method for operating the screen and heating element and determining a degradation of a particulate filter located in the exhaust passage.
Figure 5:
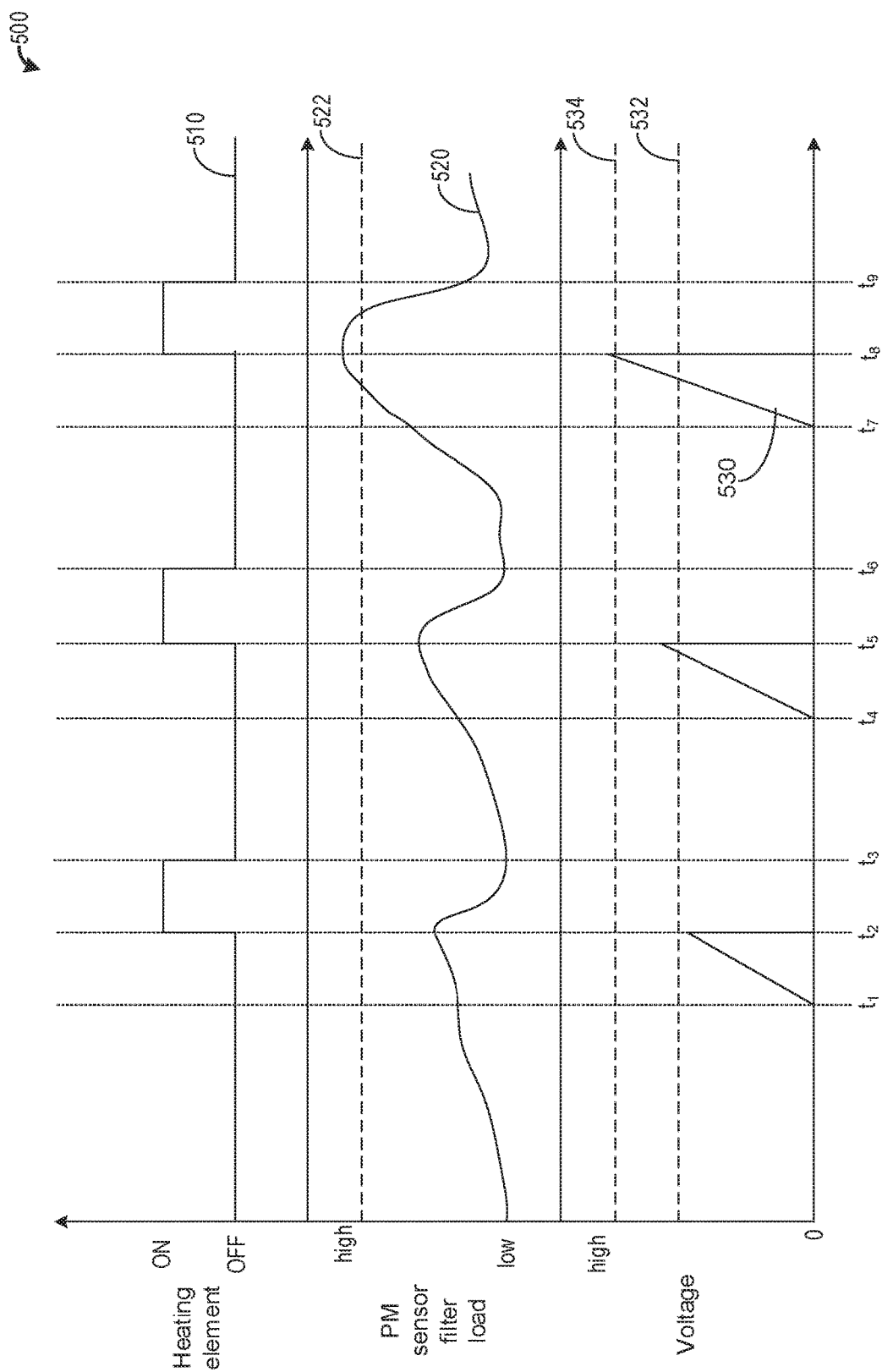
FIG. 5 shows an engine operating sequence illustrating PM sensor condition changes over time.

Turning now to FIG. 4, a method 400 for rotating the screen and diagnosing a condition of a particulate filter in an exhaust passage is shown. Instructions for carrying out method 400 and the rest of the methods included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

Components previously introduced may be integrated with the description of the method 400 described herein. For example, the screen 254, the filter 256, the heating element 258, the PM sensor 106, the particulate filter 104, the actuator 304, the rotating shaft 306, and controller 12 of FIGS. 1, 2, and 3A.

The method 400 may begin at 402, where the method 400 includes determining, estimating, and measuring current engine operating parameters. Current engine operating parameters may include one or more of engine speed, engine temperature, vehicle speed, manifold pressure, EGR flow rate, throttle position, ambient temperature, and air/fuel ratio.

At 404, the method 400 includes determining a time elapsed since a previous rotation of the screen. In one example, the time elapsed is independent of vehicle operating parameters. As such, the time elapsed may include engine off and/or vehicle off durations. Alternatively, the time elapsed may track durations of time where the engine is on and particulate matter is emitted from the engine. As such, the time elapsed may not monitor engine off and/or vehicle off events. Additionally or alternatively, the time elapsed may not include cold-starts. Particulate matter released during a duration of a cold-start may be considerably greater than particulate matter released from an engine operating at a desired operating temperature for a similar duration.

In one example, if a vehicle is turned on and a cold-start is occurring, the particulate matter filter and PM sensor capture particulate matter. Once the cold-start is determined to be complete based on an engine temperature being greater than or equal to the desired operating temperature (e.g., 185-210° C.), then the controller may signal to the heating element in the PM sensor to regenerate the filter. Following regeneration of the filter in the PM sensor subsequent the cold-start, the controller may begin measuring a time elapsed to determine when to rotate the screen in the PM sensor.

At 406, the method includes determining if the time elapsed is greater than or equal to a threshold interval. In one example, the threshold interval is based on a fixed period interval. For example, the threshold interval is exactly equal to 10 minutes. Additionally or alternatively, the threshold interval may be based on a number of miles driven (e.g., 5 miles) since a previous rotation. Additionally or alternatively, the threshold interval may be based on an estimation of particulate matter released to the PM sensor, wherein the threshold interval is reached once the estimation is substantially equal to a threshold particulate matter released. In one example, the threshold particulate matter released is based on an amount of particulate matter released to the PM sensor from a non-degraded particulate matter filter while an engine is operating at the desired operating temperature.

If the time elapsed is less than the threshold interval, then the method 400 proceeds to 408 to maintain current engine operating parameters and does not rotate the screen. As such, power is not supplied to the actuator and the heating element is not activated. The time elapsed continues to be measured.

If the time is greater than or equal to the threshold interval then the method 400 proceeds to 410 to signal to the actuator to actuate the rotational shaft to rotate the screen a threshold angle. The threshold angle may be an angular range between 2-30 degrees. In one example, the threshold angle is exactly 5 degrees. As described above, the threshold angle (e.g., α) is measured from a starting position of the screen in a clockwise direction. In the example of method 400 herein, the actuator is an electric actuator and a voltage needed to rotate the screen is measured. However, the actuator may be a mechanical actuator and a force needed to rotate the screen may be measured without departing from the scope of the present disclosure.

At 412, the method 400 includes measuring the voltage needed to rotate the screen the threshold angle. The voltage may vary based on an amount of particulate matter stored on the filter. For example, as the particulate matter load on the filter increases, then the voltage needed to rotate the screen the threshold angle increases. Likewise, as the particulate matter load on the filter decreases, then the voltage needed to rotate the screen the threshold angle decreases. In this way, as more particulate matter is leaked through the particulate filter in the exhaust passage and flows to the filter in the PM sensor, then the voltage needed to rotate the screen increases.

At 414, the method 400 includes rotating the screen back to the starting position. This includes rotating the screen in a counterclockwise direction by an amount opposite the threshold angle. For example, if the threshold angle is 5°, then the screen is rotated −5° following measuring the voltage needed.

At 416, the method 400 includes determining if the voltage measured is less than a threshold voltage. The threshold voltage corresponds to a voltage needed to rotate the screen the threshold angle when the particulate filter upstream of the PM sensor is leaking. During rotations of the screen when the particulate filter is not leaking, the voltage needed to rotate the screen is less than the threshold voltage. However, once the particulate filter begins to leak, and the filter in the PM sensor captures an increased amount of PM, the voltage increases to the threshold voltage. Said another way, the degraded particulate matter filter leaks a sufficient amount of particulate matter over the threshold interval that the voltage needed to rotate the screen exceeds the threshold voltage.

As an example for a particulate filter in an exhaust passage upstream of the PM sensor, a relatively small amount of PM may flow through the particulate filter and to the filter in the PM sensor. The screen is rotated periodically based on the fixed interval, where the voltage needed to rotate the screen the threshold angle is substantially constant. For example, the voltage needed to rotate the screen the threshold angle when the particulate filter is not leaking is substantially equal to a lower threshold voltage (e.g., 5 V). Over time, the particulate filter may develop leaks or cracks due to high exhaust gas and/or regeneration temperatures, which may result in a greater amount of PM leaking through the particulate filter. As such, the voltage needed to rotate the screen the threshold angle increases to an upper threshold voltage (e.g., 7.5 V). In one example, the voltage needed to rotate the screen the threshold angle when the particulate filter is leaking is exactly 1.5 times greater than the voltage needed when the particulate filter is not leaking. Thus, the increased PM load on the filter in the PM sensor increases a resistance (e.g., friction) experienced by the screen during its rotation toward the threshold angle.

If the voltage is greater than or equal to the threshold voltage, then the method 400 proceeds to 418 to indicate the particulate filter in the exhaust passage upstream of the PM sensor is degraded, where the degradation may include a crack, leak, and/or hole. At 420, the method 400 further includes activating an indicator lamp to alert a vehicle operator of the degradation. This may include setting a diagnostic code and/or providing a message or illumination to an operator via a display of a vehicle in which the PM sensor is mounted. For example, the message may sent to a navigation screen of the vehicle. Additionally or alternatively, the method 400 may further include adjusting one or more engine operating parameters to decrease particulate matter emissions. This may include one or more of increasing EGR flow, increasing an air/fuel ratio, decreasing a fuel injection volume and/or pressure, and increasing in-cylinder water injections.

At any rate, the method 400 proceeds to 422 following 420 or following determination of the voltage measured being less than the threshold voltage at 416. At 422, the method 400 includes activating the heating element for a threshold regeneration duration. By activating the heating element, the filter in the PM sensor is reset to a less loaded state. Said another way, PM burns off the filter and an amount of PM on the filter decreases. In this way, a PM load is reset to a relatively low and/or zero PM load condition following each rotation of the screen.

At 424, the method 400 includes determining if the threshold regeneration duration is complete. The threshold regeneration duration may be based on an amount of time needed to burn off an amount of PM accumulated onto the filter in the PM sensor between rotations of the screen for a particulate filter that is not leaking. In one example, the threshold regeneration duration is based on a threshold amount of time (e.g., 30 seconds). Alternatively, the threshold regeneration duration is based on a threshold distance (e.g., one mile). In some examples, the threshold regeneration duration is based on a temperature measured downstream of the filter in the connecting pipe, wherein if the temperature is less than a threshold regeneration temperature (e.g., less than 600° C.), then the threshold regeneration duration is complete. If the threshold regeneration duration is not complete, then the method 400 proceeds to 426 to maintain the heating element on and continues to monitor the regeneration duration.

If the threshold regeneration duration is complete, then the method 400 proceeds to 428 to deactivate the heating element. By doing this, the filter in the PM sensor may accumulate PM without burning it off. At 430, the method 400 includes beginning to monitor time between rotations. In this way, the filter in the PM sensor is given an entirety of the threshold interval to capture PM prior to the subsequent rotation of the screen.

Turning now to FIG. 5, it shows an operating sequence 500 illustrating fixed period rotations of the screen and regenerations of the filter in the PM sensor. In one example, the operating sequence 500 is a graphical illustration of the method 400 of FIG. 4 implemented in the vehicle system 6 of FIG. 1. Plot 510 represents a condition of the heating element, which may be adjusted between ON and OFF positions. Plot 520 represents a PM sensor filter load and plot 522 represents a threshold PM sensor filter load. In one example, the threshold PM sensor filter load is based on an amount of PM accumulated onto the PM sensor filter when the particulate filter in the exhaust passage is degraded (e.g., leaking). Plot 530 represents a voltage needed to rotate the screen the threshold angle, plot 532 represents a lower threshold voltage which is substantially equal to an average voltage needed to rotate the screen when the particulate filter in the exhaust passage is not leaking, and plot 534 represents an upper threshold voltage which is substantially equal to a voltage needed to rotate the screen when the particulate filter in the exhaust passage is leaking. In some examples, the lower and upper threshold voltages may be adjusted based on engine operating parameters. For example, the lower and upper threshold voltages may be similarly increased if an engine temperature is lower than an ambient temperature (e.g., cold-start). The upper threshold voltage may be 1.5 to 3 times greater than the lower threshold voltage. In one example, the upper threshold voltage is exactly 1.5 times greater than the lower threshold voltage. As an example, if the lower threshold voltage is 10 V, then the upper threshold is 15 V. Time increases from a left side to a right side of the figure.

Prior to $t_1$, the heating element is off (plot 510) and the voltage (plot 530) is less than the lower threshold voltage (plot 532). Specifically, the voltage is substantially 0 and the screen is not being rotated. It will be appreciated that when plot 530 is occluded from the plot 500, the voltage is substantially equal to 0. The PM sensor filter load (plot 520) increases toward the threshold PM sensor filter load (plot 522) as exhaust gas flows from a portion of the exhaust passage downstream of a particulate filter to the PM sensor filter. At $t_1$, a duration since a previous screen rotation is greater than or equal to a threshold interval. As such, power (e.g., electricity) is delivered to the actuator to rotate the screen. The PM sensor filter load continues to increase and the heating element remains off.

After $t_1$ and prior to $t_2$, the voltage continues to increase toward the lower threshold voltage. The PM sensor filter load continues to increase and the heating element remains inactive. At $t_2$, the screen has rotated the threshold angle and the voltage is slightly less than the lower threshold voltage. In this way, the particulate filter in the exhaust passage is determined to be functioning as desired and is not degraded. The screen is returned to its original position and is no longer rotating. As such, voltage to the actuator coupled to the screen is decreased to zero. The heating element is activated.

After $t_2$ and prior to $t_3$, the heating element remains active and the PM sensor filter load begins to decrease to a relatively low load as PM burns off the filter. At $t_3$, the threshold regeneration duration is complete and the heating element is deactivated. In this way, the regeneration is terminated when the heating element is deactivated. In some examples, the regeneration may continue following deactivation of the heating element. As such, a self-burn occurs and the PM load on the filter continues to decrease.

After $t_3$ and prior to $t_4$, the PM sensor filter load increases as exhaust gas containing PM flows through the PM sensor. At $t_4$, the threshold interval between rotations is reached and the screen begins to rotate. As such, power is delivered to the actuator to rotate the screen. The PM sensor filter load continues to increase.

After $t_4$ and prior to $t_5$, the voltage increases to a voltage greater than the lower threshold voltage as the screen is rotated toward the threshold angle. The PM sensor filter load continues to increase. The heating element remains deactivated. At $t_5$, the screen has been rotated to an angle substantially equal to the threshold angle. The voltage needed is greater than the lower threshold voltage, but lower than the upper threshold voltage. As such, the particulate filter in the exhaust passage upstream of the PM sensor is not degraded. The screen is returned to its starting position prior to the rotating and the heating element is activated.

After $t_5$ and prior to $t_6$, the heating element remains on and the PM sensor filter load continues to decrease. At $t_6$, the threshold regeneration duration is met and the heating element is deactivated. In one example, the threshold regeneration duration is fixed and is the equal for each regeneration of the PF sensor filter. In this way, the threshold regeneration duration is independent of the PM sensor filter load. The PM sensor filter load is decreased to a relatively low load, similar to a PM load at $t_3$. Thus, the heating element returns the PM sensor filter a similar condition following each regeneration of the PM sensor filter.

In another example, the threshold regeneration duration from $t_5$ to $t_6$ is longer than the threshold regeneration duration between $t_2$ and $t_3$. This may be due to the PM sensor filter load being greater at $t_5$ than at $t_2$, which may be determined by the voltage needed to rotate the screen. Said another way, the threshold regeneration duration may be proportional to the voltage needed to rotate the screen to the threshold angle. Thus, as the voltage needed increases, the threshold regeneration also increases.

After $t_6$ and prior to $t_7$, the PM sensor filter load begins to increase from the relatively low load toward the threshold PM sensor filter load. At $t_7$, the screen begins to rotate and the actuator coupled to the screen receives power.

After $t_7$ and prior to $t_8$, the screen continues to rotate. The PM sensor filter load continues to increase and increases to a load greater than the threshold PM sensor filter load. As described above, the threshold PM sensor filter load corresponds to an amount of PM creating enough friction that a voltage needed to rotate the screen to the threshold angle exceeds the upper threshold voltage. At $t_8$, the screen reaches the threshold angle and the voltage needed to rotate the screen exceeds the upper threshold voltage. As a result, the particulate filter in the exhaust passage upstream of the PM sensor is determined to be degraded, wherein the degradation includes one or more of a leak and a crack. As such, a flag is set and an indicator lamp is activated to notify a vehicle operator of the degraded particulate filter. Power is no longer supplied to the actuator coupled to the screen. The heating element is activated.

After $t_8$ and prior to $t_9$, the heating element continues to regenerate the PM sensor filter. In some examples, additionally of alternatively, one or more engine operating parameters may be adjusted to reduce PM output from the engine in light of the particulate filter being degraded. For example, an EGR flow rate to the engine may increase in response to the particulate filter being degraded. Additionally or alternatively, an amount of fuel injected into one or more of the engine cylinders may be reduced (e.g., an air/fuel ratio may increase). At $t_9$, the threshold regeneration duration is reached and the heating element is deactivated. Following $t_9$, the PM sensor filter load continues to increase.

Turning now to FIG. 6, it shows a second embodiment 600 of the PM sensor 106 of FIG. 1. In one example, the second embodiment 600 is similar to the first embodiment 200 depicted in FIG. 2. Specifically, the second embodiment 600 comprises the upstream pipe 222, perforations 224, downstream pipe 232, outlet 234, connecting pipe 242, filter 256, and heating element 258 depicted in the first embodiment 200. Furthermore, the second embodiment 600 may be arranged in a similar portion of the exhaust passage 35 as the first embodiment 200. Additionally, exhaust gas flow through the second embodiment 600 is substantially similar to exhaust gas flow through the first embodiment 200.

However, the second embodiment 600 differs from the first embodiment 200 in that it does not include a screen (e.g., screen 254 of FIG. 2). Thus, the second embodiment 600 also does not include the actuators described above for rotating the screen. The second embodiment 600 further comprises a first sensor 612 and a second sensor 614 that are not depicted in the first embodiment 200.

In one example, the first sensor 612 and the second sensor 614 are temperature sensors. Herein, the first sensor 612 is referred to as a first temperature sensor 612. Likewise, the second sensor 614 is referred to as a second temperature sensor 614. The first temperature sensor 612 is upstream of the second temperature sensor 614 relative to a direction of exhaust gas flow. The filter 256 and heating element 258 are located between the first 612 and second 614 temperature sensors. In this way, the first temperature sensor 612 measures a temperature of exhaust gas in the PM sensor 106 upstream of the filter 256. Additionally, the second temperature sensor 614 measures a temperature of exhaust gas in the PM sensor 106 downstream of the filter 256 and heating element 258. Controller 12 comprise instructions stored thereon that when executed enable the controller to determine a temperature change across the filter 256 based on feedback from the first 612 and second 614 temperature sensors. In one example, the temperature change is measured only when the heating element is activated. The heating element may be activated based on a fixed period interval, as will be described in greater detail below.

In some examples, additionally or alternatively, the first embodiment 200 and the second embodiment 600 may be combined such that the PM sensor includes the rotatable screen and the temperature sensors. In such an embodiment, a routine for diagnosing a particulate matter filter in an exhaust passage upstream of the PM sensor may include monitoring a power needed to rotate the screen the threshold angle and measuring a temperature change across the filter of the PM sensor. In one example, if the power needed is greater than a threshold power or if the temperature change is greater than the threshold temperature change, then the particulate matter filter in the exhaust passage is degraded.

Turning now to FIG. 7, it shows a method 700 for periodically regenerating the filter and measuring a temperature change of exhaust gas across the filter in response to the regeneration. In one example, the method 700 may be executed with respect to the second embodiment 600 of the PM sensor 106.

In some examples, the method 700 be implemented in conjunction with the method 400 described above. Specifically, for an embodiment comprising features of the first 200 and second 600 embodiments, the method 700 may begin following rotation of the screen from the threshold angle position back to its starting position (e.g., box 414). In such an example, the method 700 may begin at 710.

The method 700 may begin at 702, where the method 700 includes determining, estimating, and measuring current engine operating parameters. Current engine operating parameters may include one or more of engine speed, engine temperature, vehicle speed, manifold pressure, EGR flow rate, throttle position, ambient temperature, and air/fuel ratio.

At 704, the method 700 includes determining a time elapsed since a previous regeneration of the filter. The time elapsed is measured from a termination of a previous regeneration. The time elapsed is substantially similar to the time elapsed and its measurement is similar to the measurement described above at 404.

At 706, the method includes determining if the time elapsed is greater than or equal to a threshold interval. In one example, the threshold interval is based on a fixed period interval. For example, the threshold interval is exactly equal to 10 minutes. Additionally or alternatively, the threshold interval may be based on a number of miles driven (e.g., 5 miles) since a previous regeneration.

If the time elapsed is less than the threshold interval, then the method 700 proceeds to 708 to maintain current engine operating parameters and does not regenerate the filter. As such, the heating element is not activated. If the time is greater than or equal to the threshold interval then the method 700 proceeds to 710 to signal the heating element to heat the filter. As such, the heating element is activated a temperature of the filter increases. In one example, the filter increases to at least a threshold regeneration temperature (e.g., 600° C.). In this way, PM stored on the filter may begin to burn, resulting in hotter exhaust gas downstream of the filter compared to upstream of the filter.

At 712, the method 700 includes measuring exhaust gas temperatures upstream and downstream of the filter in the PM sensor. The first temperature sensor 612 measures an exhaust gas temperature upstream of the filter and the second temperature sensor 614 measures an exhaust gas temperature downstream of the filter. It will be appreciated that a temperature measured by the second temperature sensor is greater than a temperature measured by the first temperature sensor. In one example, measuring the exhaust gas temperature may be delayed following activation of the heating element for a threshold time (e.g., 15 seconds following activation of the heating element). Additionally or alternatively, temperatures may be measured by the first and second temperature sensors throughout a heating of the filter and a largest temperature difference between the first and second temperature sensors may be used in a remainder of the method 700.

At 714, the method 700 includes determining if a temperature difference between the first and second temperature sensors is less than at a threshold temperature difference and/or threshold temperature change. The threshold temperature difference is based on a temperature difference between the sensors when the particulate filter in the exhaust passage upstream of the PM sensor is leaking. The threshold temperature difference is greater than an average temperature difference between the first and second temperature sensors when the PF is not leaking. In one example, the threshold temperature difference is exactly 1.5 times greater than the average temperature difference. Other magnitudes between the threshold temperature difference and average temperature difference have been realized.

Said another way, regeneration of the filter in the PM sensor occurs at a first temperature, wherein the first temperature is a regeneration temperature based on an amount of particulate matter capture by the filter following the threshold interval. If the particulate matter filter in the exhaust passage is degraded, then an amount of particulate matter captured by the filter during the threshold interval is greater than the amount captured when the particulate matter filter is not degraded. As such, regeneration of the filter in the PM sensor when the particulate matter filter is degraded occurs at a second temperature, which may be greater than the first temperature. If a temperature difference between feedback from the first temperature sensor 612 and the second temperature sensor 614 is greater than the threshold change (e.g., the regeneration is too hot from too much particulate matter burning), then the particulate matter filter is degraded.

If the temperature difference if greater than the threshold temperature difference, then the method 700 proceeds to 716 to signal that the particulate filter in the exhaust passage is degraded. At 718, an indicator lamp is activated to signal to the driver that maintenance is desired.

At any rate, the method 700 proceeds to 720 following 718 or following determination that the threshold change is less than the threshold temperature change to continue heating the filter.

At 722, the method 700 includes determining if the threshold regeneration duration is complete. The threshold regeneration duration at 722 is similar to the threshold regeneration duration previously described at 424 of method 400.

If the threshold regeneration duration is not complete, then the method proceeds to 724 to continue monitoring the regeneration duration. If the threshold regeneration duration is complete, then the method proceeds to 726 to deactivate the heating element. Following deactivation of the heating element, the method 700 begins to monitor time between regenerations at 728.

In an alternative embodiment, wherein a PM sensor comprises both the screen and the temperature sensors described above, a method may include rotating the screen and subsequently measuring a temperature change across the filter during a regeneration. As such, the method may include monitoring a time elapsed between rotations of the screen, wherein the screen is rotated when the time elapsed is substantially equal to a threshold interval. The screen is rotated to the threshold angle, and then returned to its starting position. An amount of power needed to rotate the screen to the threshold angle is measured. Following return of the screen to its starting position, the heating element is activated and exhaust gas temperatures upstream and downstream of the filter are measured.

In one example, if both the power needed to rotate the screen is greater than a threshold power and a temperature change across the filter is greater than a threshold temperature change, then the particulate matter sensor located in the exhaust passage is determined to be degraded. Additionally or alternatively, if only one of the power needed to rotate the screen is greater than the threshold power or the temperature change across the filter is greater than the threshold temperature change, then the particulate matter filter in the exhaust passage is determined to be degraded. In some examples, the particulate filter in the exhaust passage is not determined to be degraded if only one or both of the power needed to rotate the screen is less than a threshold power and the temperature change across the filter is less than a threshold temperature change.

Turning now to FIG. 8, it shows an operating sequence 800 illustrating fixed period regenerations of the filter in the PM sensor. In one example, the operating sequence 800 is a graphical illustration of the method 700 of FIG. 7 implemented in the vehicle system 6 of FIG. 1. Plot 810 represents a condition of the heating element, which may be adjusted between ON and OFF positions. Plot 820 represents a PM sensor filter load and plot 822 represents a threshold PM sensor filter load. In one example, the threshold PM sensor filter load is based on an amount of PM accumulated onto the PM sensor filter when the particulate filter in the exhaust passage is degraded (e.g., leaking). Plot 830 represents a temperature change measured between first 612 and second 614 temperature sensors, plot 832 represents a lower threshold temperature change which is substantially equal to an average temperature change measured when the particulate filter in the exhaust passage is not leaking, and plot 834 represents an upper threshold temperature change which is substantially equal to a temperature change measured when the particulate filter in the exhaust passage is leaking. In some examples, the lower and upper threshold temperature changes may be adjusted based on engine operating parameters. For example, the lower and upper threshold temperature changes may be similarly increased if engine temperature is lower than an ambient temperature (e.g., cold-start). The upper threshold temperature change may be 1.5 to 3 times greater than the lower threshold temperature change.

Prior to $t_1$, the heating element is off (plot 810) and the temperature change (plot 830) is less than the lower threshold temperature change (plot 832). Specifically, the temperature change is substantially 0 and the PM sensor filter is not being regenerated. It will be appreciated that when plot 830 is occluded from the plot 800, the temperature change is substantially equal to 0. The PM sensor filter load (plot 820) increases toward the threshold PM sensor filter load (plot 822) as exhaust gas flows from a portion of the exhaust passage downstream of a particulate filter to the PM sensor filter. At $t_1$, a duration since a previous regeneration is greater than or equal to a threshold interval. As such, the heating element is activated to initiate a regeneration and the PF load begins to decrease. Additionally, the temperature change begins to increase as exhaust gas downstream of the filter is hotter than exhaust gas upstream of the filter due to the regeneration.

After $t_1$ and prior to $t_2$, the heating element remains active and the PM sensor filter load begins to decrease to a relatively low load as PM burns off the filter. At $t_2$, the temperature change is substantially equal to the lower threshold temperature change. In this way, the particulate filter in the exhaust passage is determined to be functioning as desired and is not degraded. Plot 800 depicts a greater temperature change occurring at the end of the regeneration. However, it will be appreciated that the highest temperature change may occur during the regeneration at any point between $t_1$ and $t_2$. The threshold regeneration duration is complete and the heating element is deactivated. In this way, the regeneration is terminated when the heating element is deactivated. In some examples, the regeneration may continue following deactivation of the heating element. As such, a self-burn occurs and the PM load on the filter continues to decrease.

After $t_2$ and prior to $t_3$, the PM sensor filter load increases as exhaust gas containing PM flows through the PM sensor. At $t_3$, the threshold interval between regenerations is met and the heating element is activated to regenerate the filter in the PM sensor. As such, a temperature change begins to develop between the first and second temperature sensors.

After $t_3$ and prior to $t_4$, the temperature change increases to a temperature change greater than the lower threshold temperature change as the PM on the filter continues to regenerate. The PM sensor filter load continues to decrease. The heating element remains activated. At $t_4$, the threshold regeneration duration is complete. A greatest temperature change is greater than the lower threshold temperature change, but lower than the upper threshold temperature change. As such, the particulate filter in the exhaust passage upstream of the PM sensor is not degraded. The heating element is deactivated.

After $t_4$ and prior to $t_5$ the PM sensor filter load begins to increase and increases to a load greater than the threshold PM sensor filter load. As described above, the threshold PM sensor filter load corresponds to an amount of PM hot regeneration temperature. As such, a change in exhaust gas temperatures across the filter will be greater than or equal to the threshold temperature change at the next regeneration. At $t_5$, a time elapsed since the previous filter regeneration is substantially equal to the threshold interval, and the regeneration is initiated. As such, the heating element is activated and the particulate matter begins to burn off the filter. The temperature change begins to increase as exhaust gas downstream of the filter gets hotter.

After $t_5$ and prior to $t_6$, the heating element remains on and the PM sensor filter load continues to decrease. The temperature change measured across the filter exceeds the upper threshold temperature change. As such, the temperature change (e.g., temperature difference between exhaust gas downstream and upstream of the filter) is similar to 1.5 times an average temperature change (e.g., the lower threshold temperature change) measured when the particulate matter filter in the exhaust passage is not degraded. At $t_6$, the threshold regeneration duration is met and the heating element is deactivated. The PM sensor filter load is decreased to a relatively low load, similar to a PM load at $t_3$. Thus, the heating element returns the PM sensor filter a similar condition following each regeneration of the PM sensor filter.

After $t_6$, the threshold regeneration duration is complete and the heating element is deactivated. The PM sensor filter load begins to increase. Additionally, the particulate matter filter is flagged as being degraded. In one example, an indicator lamp is activated to notify a driver of the degradation. Additionally or alternatively, the engine operating parameters are adjusted to decrease PM output from the engine, as described above.

In this way, a particulate matter sensor located downstream of a particulate matter filter may diagnose a condition of the particulate matter filter based on one or more of friction and temperature. In one example, the particulate matter sensor includes a rotatable screen configured to demand a greater amount of power as particulate matter stored on a filter of the sensor becomes increasingly loaded with particulate matter. Additionally or alternatively, the particulate matter sensor includes a pair of temperature sensor located upstream and downstream of the filter. A temperature difference between the two sensors is greater during regenerations of the filter comprising where a greater amount of particulate matter is stored on the filter. The technical effect of monitoring a particulate matter filter in an exhaust passage via friction and/or temperature changes is to accurately monitor particulate matter leaking through the particulate matter filter via a compact and easy-to-manufacture particulate matter sensor.

A method comprising rotating a screen of a particulate matter sensor periodically via an actuator and indicating leakage of a particulate filter based on an amount of power supplied to the actuator. A first example of the method further includes where the screen is pressed against a filter of the particulate matter sensor, wherein the screen is rotated periodically responsive to operating conditions of the engine and/or exhaust system, and wherein the indication includes setting a diagnostic code and/or providing a message or illumination to an operator via a display of a vehicle in which the sensor is mounted. A second example of the method, optionally including the first example, further includes where the rotating comprises supplying power to the actuator to rotate the screen between 2 to 15 degrees. A third example of the method, optionally including the first and/or second examples, further includes where the rotating is performed at fixed period intervals. A fourth example of the method, optionally including one or more of the first through third examples, further includes where the leakage is determined based on a determination of the amount of power exceeding a threshold power.

An embodiment of a method comprising heating a filter of a particulate matter sensor in an engine exhaust and indicating leakage of a particulate filter based on a temperature difference of exhaust gas upstream and downstream of the filter. A first example of the method optionally includes where the particulate matter sensor is coupled to a first temperature sensor upstream of the filter and a second temperature sensor downstream of the filter relative to a direction of incoming exhaust gas flow. A second example of the method optionally including the first example further includes where the heating is performed at regular intervals. A third example of the method, optionally including the first and/or second examples, further includes where the temperature difference is equal to 1.5 times a regeneration temperature of the filter.

An embodiment of a system comprising an exhaust passage having a particulate filter and a particulate matter sensor located downstream of the particulate filter relative to a direction of exhaust gas flow, and where the particulate matter sensor is coupled with an upstream pipe, a downstream pipe, and a connecting pipe physically coupled to one another in a U-shape. A first example of the system further includes where the upstream pipe comprises a plurality of perforations for admitting exhaust gas into the particulate matter sensor. A second example of the system, optionally including the first example, further includes where the downstream pipe comprises an outlet for expelling exhaust gas into the exhaust passage. A third example of the system, optionally including the first and/or second examples, further includes where the connecting pipe is located completely outside of the exhaust passage. A fourth example of the system, optionally including one or more of the first through third examples, further includes where the upstream pipe and downstream pipe are perpendicular to a central axis of the exhaust passage. A fifth example of the system, optionally including one or more of the first through fourth examples, further includes where the connecting pipe is parallel to the central axis. A sixth example of the system, optionally including one or more of the first through fifth examples, further includes where the particulate matter sensor is asymmetric, and where the upstream pipe extends further into the exhaust passage than the downstream pipe. A seventh example of the system, optionally including one or more of the first through sixth examples, further includes where the connecting pipe comprises a filter configured to capture particulate matter and a heating element for heating the filter. An eighth example of the system, optionally including one or more of the first through seventh examples, further includes where the heating element heats the filter periodically based on a fixed time interval, and where the connecting pipe further comprises first and second temperature sensor upstream and downstream of the filter, respectively, and where a degradation of the particulate filter is determined based on a temperature difference between the first and second temperature sensors. A ninth example of the system, optionally including one or more of the first through eighth examples, further includes where the connecting pipe further comprises a screen pressed against the filter, and where the screen is configured to rotate periodically via an actuator, and where a degradation of the particulate filter is determined based on a threshold voltage consumed by the actuator to rotate the screen. A tenth example of the system, optionally including one or more of the first through ninth examples, further includes where the particulate matter sensor comprises no additional inlets or other outlets other than perforations located on the upstream pipe and outlet located on the downstream pipe.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the engine control system, where the described actions are carried out by executing the instructions in a system including the various engine hardware components in combination with the electronic controller.

Note that FIGS. 2 and 6 show arrows indicating where there is space for gas to flow, and the solid lines of the device walls show where flow is blocked and communication is not possible due to the lack of fluidic communication created by the device walls spanning from one point to another. The walls create separation between regions, except for openings in the wall which allow for the described fluid communication.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method comprising:
   rotating a screen of a particulate matter sensor periodically via an actuator; and
   indicating leakage of a particulate filter based on an amount of power supplied to the actuator.

2. The method of claim 1, wherein the screen is pressed against a filter of the particulate matter sensor, wherein the screen is rotated periodically responsive to operating conditions of an engine and/or exhaust system, and wherein the indicating includes setting a diagnostic code and/or providing a message or illumination to an operator via a display of a vehicle in which the particulate matter sensor is mounted.

3. The method of claim 1, wherein the rotating comprises supplying power to the actuator to rotate the screen between 2 to 15 degrees.

4. The method of claim 1, wherein the rotating is performed at fixed period intervals.

5. The method of claim 1, wherein the leakage is determined based on a determination of the amount of power exceeding a threshold power.

* * * * *